United States Patent [19]
Johnson

[11] Patent Number: 6,040,913
[45] Date of Patent: Mar. 21, 2000

[54] METHOD TO DETERMINE LIGHT SCATTERING EFFICIENCY OF PIGMENTS

[75] Inventor: Robert William Johnson, Kennett Square, Pa.

[73] Assignee: E. I. du Pont de Nemours and Company, Wilmington, Del.

[21] Appl. No.: 09/240,251

[22] Filed: Jan. 29, 1999

[51] Int. Cl.[7] .................................................. C10D 8/23
[52] U.S. Cl. ..................... 356/432; 356/436; 356/441; 106/436
[58] Field of Search .................................... 356/432, 336, 356/338, 339; 106/436, 437

[56] References Cited

U.S. PATENT DOCUMENTS

| | | | |
|---|---|---|---|
| 5,632,273 | 5/1997 | Suzuki | 128/633 |
| 5,650,002 | 7/1997 | Bolt | 106/438 |
| 5,653,793 | 8/1997 | Ott et al. | 106/437 |
| 5,717,494 | 2/1998 | Taguchi et al. | 356/432 |
| 5,886,069 | 3/1999 | Bolt | 523/223 |
| 5,922,120 | 7/1999 | Subramanian et al. | 106/437 |

*Primary Examiner*—Robert H. Kim
*Assistant Examiner*—Layla Lauchman

[57] ABSTRACT

A method for determining light scattering efficiency and a method to determine undertone of pigments are described. The methods are based on measuring total transmittance of pigment slurries at a wavelength of at least 600 nm. Transmittance measurements can be used to calculate light scattering efficiencies and undertone which correlate with performance in end-use applications.

16 Claims, 2 Drawing Sheets

METHOD TO DETERMINE LIGHT SCATTERING EFFICIENCY OF PIGMENTS

BACKGROUND OF THE INVENTION

1. Field of the Invention

This invention relates to a method of measuring light scattering efficiency of white pigments.

2. Description of the Related Art

Light scattering properties are the primary product attributes of white pigments, particularly $TiO_2$ pigments. Precise, accurate evaluations of light scattering properties of pigments are important to guide product development, improve control of the manufacturing process, and aid consumers as they optimize use of pigments.

Two key properties in essentially all end-use applications of white pigments are (a) scattering efficiency for delivering opacity, which relates to hiding power and tint strength; and (b) undertone, which relates to the change of scattering efficiency as the wavelength of light varies. Opacity is the ability of a pigment to mask the features of the underlying substrate. Undertone of a white pigment may be described as the hue (bluish or reddish) of a gray paint containing the pigment in an admixture with a standard black pigment. Generally, a bluish undertone is characteristic of small particle size, while a reddish undertone is characteristic of larger and less uniform particle size. Undertone is particularly important in applications where color matching is needed.

Light scattering properties are typically measured on end-use products or lab simulations of end-use applications. Such measurement procedures are often complex, time-consuming and subject to errors due to variability in raw materials, variability introduced by having a multi-step process, and operator variability. Therefore, product characterization and process control have generally focused on fundamental properties, such as particle size measurements. Correlations between particle size and end-use properties are often used to infer actual optical properties of the pigments. Most particle size analyzers report particle sizes based on theoretical equations that assume a spherical shape. Therefore, the reported sizes are equivalent spherical diameters. However, pigments can have complex microstructures. For example, $TiO_2$ pigments contain twinned and aggregated primary crystals and non-spherical particles. Further, most commercial grades of $TiO_2$ pigments have hydrous oxide coatings. Therefore, measurements of equivalent spherical diameters may not accurately predict end-use performance of a pigment.

Pigments provide opacity or hiding power by diffuse light scattering in end-use applications. Measurements of opacity that do not include the diffuse component of transmittance do not provide results that reliably correlate with end-use properties.

Heretofore, scattering efficiency has typically been measured at a green light wavelength (540–580 nm) in the center of the visible spectrum where the eye is most sensitive. Undertone characterizes the change of scattering efficiency across the visible spectrum and therefore has been determined by comparing scattering efficiency at a blue wavelength relative to scattering efficiency at a red wavelength of light. Test methods in the prior art characterize pigments by (1) measurements on the end-use or a lab simulation of the end-use application, or (2) measurements on slurries of the pigment.

As an example of the first type, Bruehlman and Ross in *J. Paint Techn.* 1969, vol. 41, pp. 584–596 disclose use of transmission measurements using a spectrophotometer with an integrating sphere to determine scattering efficiency. Measurements are taken at 5500 Å (550 nm) of $TiO_2$ coating formulations deposited on plastic sheets. An improvement to the method of Bruehlman and Ross was described by Abrams, et al., in "Proceedings of 1996 TAPPI Coating Conference", TAPPI Press, Atlanta, Ga., 1996, pp. 185–192. For applications where $TiO_2$ is used in porous media, e.g., paper coatings or paint films formulated above the critical pigment volume concentration, Abrams, et al. incorporate information on the porosity of the coating into calculations of hiding power.

As an example of the second type, Losoi in "Proceedings of 5th International Paint Congress", Sao Paulo, Brazil, Sep. 15, 1997, p. 213 (ABRAFATI, Brazilian Association of Paint Manufacturers, Rua Augusta, 2516-2° andar -cj.22-01412-100-Sao Paulo-SP) describes methods for determining optical properties of $TiO_2$ pigments dispersed in water. These pigments are aggregates of smaller primary crystals. Absorbance of a dilute slurry at 550 nm is used as a predictor of gloss properties. It also gives some indication of hiding power or tint strength, but correlations are limited unless independent information is available on the primary crystal size. A method for measuring undertone is based on the ratio of absorbance measurements of a dilute slurry of $TiO_2$ at 400 and 700 nm.

Turnstall, U.S. Pat. No. 4,279,512 discloses a method for measuring mean particle size of particles suspended in a continuous medium which involves measuring non-scattered radiation which passes through the continuous medium at three different wavelengths, R1, R2 and R3. Attenuation ratios are determined from the measurements. The attenuation ratios are compared with a set of previously calculated attenuation ratios for a selection of mean particle sizes, corresponding to the determined attenuation ratios. Use of the method to measure mean particle size of $TiO_2$ particles in aqueous suspension is disclosed.

Methods based on characterization of pigment slurries have major advantages over methods that require preparation of the end-use product: they are faster, less expensive, and can normally be determined with much higher precision. But prior art methods using pigment slurries have had limitations that restrict their ability to give results which directly correlate with performance in end-use applications.

Scattering performance is very sensitive to the difference between the refractive index of the pigment particle and the refractive index of the medium around the particle. The refractive index of water is low compared to the refractive index of the medium in end-use applications. Therefore measurements of optical properties of aqueous slurries of pigments in the blue-green region of the visible spectrum (450–600 nm) may provide inaccurate information regarding performance in an end-use medium.

SUMMARY OF THE INVENTION

This invention provides a method to determine pigment properties that correlate with performance of a pigment in an end-use application where the pigment is dispersed, for example, in a paint or coating. This invention provides a rapid, precise method that directly provides light scattering efficiency of a pigment, which comprises:

(a) preparing a dilute slurry of a pigment in a continuous liquid medium having a known concentration (C), where concentration is the concentration of pigment in the slurry;

(b) measuring total transmittance (T) of the slurry at a wavelength ($\lambda$) of at least 600 nm;

(c) converting the transmittance measurement (T) to optical density (OD) by the equation $$OD = -\log(T)$$

and (d) dividing the optical density by the concentration (C) of the pigment in the slurry to determine light scattering efficiency of the pigment.

In particular, the method of this invention can be used to determine light scattering efficiency of a number of white pigments. Preferably the pigment is selected from the group consisting of both rutile and anatase titanium dioxide, zinc oxide, silica, calcium carbonate, calcium sulfate and clay, and mixtures thereof. More preferably, the pigment is rutile or anatase titanium dioxide ($TiO_2$).

This invention further provides a method to determine pigment undertone, which comprises:

(a) preparing a dilute slurry of pigment particles in a continuous liquid medium having a known concentration (C), where concentration is the concentration of pigment in the slurry;

(b) measuring the total transmittance ($T_1$) of the slurry at a first wavelength, $\lambda_1$, between 500 and 600 nm;

(c) measuring the total transmittance ($T_2$) of the slurry at a second wavelength, $\lambda_2$, between 600 and 1000 nm;

(d) converting the transmittance measurements to optical densities (OD) by the equation $$OD = -\log(T)$$

(e) dividing the optical densities by the concentration (C) of the pigment in the slurry to calculate OD/C;

(f) determining undertone of the pigment by the degree of change in OD/C between $\lambda_1$ and $\lambda_2$.

A number of equations can be used to determine undertone, or the change in OD/C between the two wavelengths, $\lambda_1$ and $\lambda_2$. Preferably, undertone is determined according to the equation:

$$\text{undertone} = -\frac{\left[\ln\dfrac{OD_1/C \text{ at } \lambda_1}{OD_2/C \text{ at } \lambda_2}\right]}{\left[\ln\dfrac{\lambda_1}{\lambda_2}\right]}.$$

$OD_1/C$ at $\lambda_1$ is the optical density calculated from the transmittance measurement at wavelength $\lambda_1$ divided by the concentration of pigment in the slurry. $OD_2/C$ at $\lambda_2$ is the optical density calculated from the transmittance measurement at wavelength $\lambda_2$ divided by the concentration of pigment in the slurry.

DETAILED DESCRIPTION OF THE INVENTION

Figure 1:
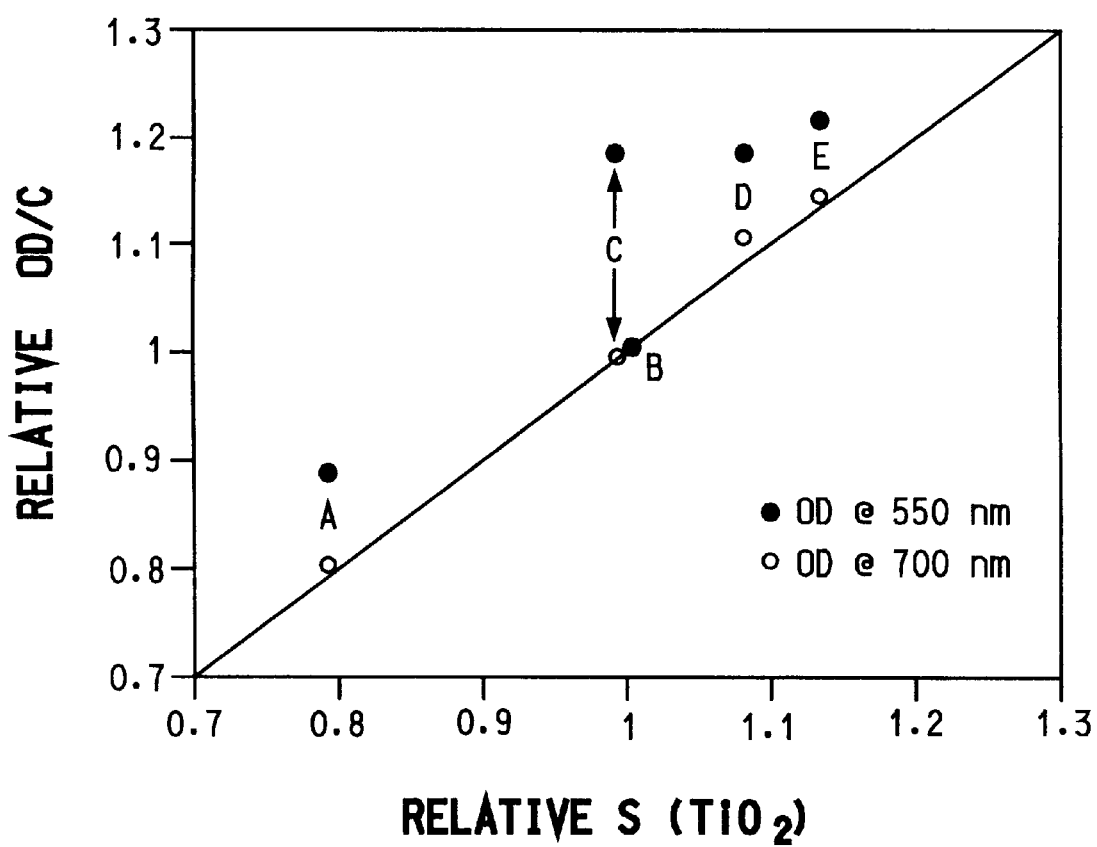
FIG. 1 is a graph showing relative optical densities for a series of pigments and the corresponding relative scattering coefficients (S) for these pigments in a paper coating.

The present invention relates to methods to determine light scattering properties of white pigments. Pigments are commonly dispersed in films or coatings in an end-use. The methods of this invention provide a rapid process to determine optical density and undertone of a pigment with the pigment dispersed in a continuous liquid medium. These methods are particularly useful to provide information that correlates to performance of the pigment in end-use applications.

Instrumentation

In this invention, a spectrophotometer is used to measure transmittance (T) through a sample of a dilute slurry of a white pigment. Optical density is calculated as $OD=-\log(T)$. While there are numerous spectrophotometers available commercially, for purposes of this invention, it is critical that the spectrophotometer provides a measure of the total transmittance of the sample. "Total transmittance" includes both regular (rectilinear or straight-through) and diffuse transmittance. Regular transmittance relates to the energy that passes directly through the sample. Diffuse transmittance relates to energy that is scattered as it passes through the sample.

Total transmittance is important in a measurement of a white pigment to correlate the results with end-use performance, since performance of a pigment in the end-use depends on diffuse scattering. For correlations of measurements with end-use, e. g., in a paper coating or a paint film, use of total transmittance at the appropriate wavelength can provide a 1:1 relationship between optical density and the light scattering efficiency (hiding power) in the end-use application. If the instrument measures only regular transmittance, some differences between pigments can be characterized, but there is no 1:1 correlation between optical density and end-use performance.

One method of obtaining measurements of total transmittance of a sample is to equip the spectrophotometer with an integrating sphere. Such a modification is available commercially. Other methods can be used to obtain measurements of total transmittance.

Sample Preparation

In the method of this invention, a dilute slurry of pigment particles in a continuous liquid medium of a known concentration is prepared. Concentration is referred to herein as the concentration of pigment in the slurry. The preferred pigments to be used in the method of this invention are commercial white pigments commonly used as opacifiers. These pigments include rutile titanium dioxide ($TiO_2$), anatase $TiO_2$, zinc oxide, silica, calcium carbonate, calcium sulfate, zinc sulfide, basic lead sulfate, basic lead carbonate, antimony oxide, lithopone or the like, and clays, e. g., kaolin clay, and mixtures thereof. Preferably the pigment is selected from the group consisting of both rutile and anatase titanium dioxide, zinc oxide, silica, calcium carbonate, calcium sulfate and clay, and mixtures thereof. Most preferably, the pigment is rutile or anatase titanium dioxide.

Typically and preferably, the continuous medium is water, however, other continuous media that can be used include other hydrophilic media or hydrophobic media such as organic solvents, or a paint resin.

The concentration of the pigment in the dilute slurry will depend on the path length of the spectrophotometer cell. The pigment concentration should be within a range of concentration where optical density is directly proportional to concentration. The concentration should also be in a sensitive range for the instrument where there is a high signal-to-noise ratio. For example, for a slurry of $TiO_2$ in water, using a cell having a path length of 1 cm, the concentration of $TiO_2$ in the slurry should be in the range of 5 to 50 ppm, preferably 10–30 ppm. For cells having a path length less than 1 cm, a higher concentration of $TiO_2$ in the slurry may be tolerated, while maintaining the linear relationship of optical density to $TiO_2$ concentration. Conversely, for cells having a path length greater than 1 cm, lower concentrations of $TiO_2$ in the slurry should be used.

For other pigments and for continuous media other than water, concentration may need to be higher or lower to satisfy the proportional relationship between optical density and concentration and also high signal-to-noise. For low refractive index pigments, such as calcium carbonate and clays, concentrations on the order of 100–300 ppm, are preferred when using water as the continuous medium. It should be recognized that one skilled in the art will be able to determine the optimum pigment concentration to use.

A dilute pigment slurry is prepared by mixing a slurry of the pigment or solid pigment with a sufficient amount of the continuous medium to provide the desired concentration. Optionally, the slurry is subjected to a pretreatment prior to dilution. Examples of pretreatment methods include grinding and sonication. Sonication is a preferred step when preparing a slurry from a dry sample. Preferably the dilute slurry will be prepared by stepwise dilution of pigment slurries of higher concentration. It is important to accurately prepare the dilute slurry sample as errors in concentration will negatively impact the accuracy of calculated results and affect the ability to correlate results with end-use performance of the pigment.

Optionally, a dispersant is added to the dilute slurry. Dispersants include polyacrylates, citric acid, boric acid, acetic acid, adipic acid, succinic acid, tetrapotassium pyrophosphate(TKPP), ethylenediaminetetraacetic acid, triethanol amine (TEA), 2-amino-2-methyl-1-propanol (AMP), trimethylol propane (TMP), or the like, and mixtures thereof.

Measurements

The dilute pigment slurry should be added to a spectrophotometer cell per instrument instructions to provide a sample.

The method of this invention can be used to determine optical properties of a white pigment, which correlate with end-use performance by measuring transmittance of a slurry containing the pigment at a wavelength of at least 600 nm, and typically from 600 to 1000 nm. The preferred wavelength for characterizing light scattering efficiency or hiding power is shifted from the green region of the spectrum (540 to 580 nm) to a higher wavelength. The shift depends on the end-use application for which the pigment is intended and the refractive index of the continuous medium in which the transmittance measurement is taken. When optical density is based on a transmittance measurement taken in water (refractive index 1.33), the preferred wavelength to use for a pigment for use in a pigment-filled paper is shifted by about 50 to 100 nm to about 600 to 700 nm. For a pigment to be used in a paper coating, when the continuous medium is water, the preferred wavelength is shifted by about 150 nm to about 650 to 750 nm, and more preferably, the wavelength is 700 nm. For a pigment to be used in a plastics application, especially when the pigment is $TiO_2$ and the $TiO_2$ concentration is less than 15%, the preferred wavelength to determine optical properties is also in the range 650 to 750 nm, when the continuous medium is water.

For a pigment to be used in coatings applications, such as in a paint, the preferred wavelength from which to determine optical properties is 750 to 1000 nm, when the continuous medium is water. This range is broader than the range for paper and plastics applications since there is greater variability in coatings formulations. The formulation may be water-based or solvent-based. Pigment volume concentration (PVC), and particularly the $TiO_2$ volume concentration, will also impact the preferred wavelength. By "$TiO_2$ volume concentration", it is meant the ratio, by volume, of $TiO_2$ pigment to the remaining components of the formulation and may be expressed by the following formula:

$$\% \ TiO_2 \ \text{Pigment} = \frac{\text{volume of } TiO_2 \ \text{Pigment}}{\text{Total volume of coating solids}} \times 100$$

For a typical latex paint having a $TiO_2$ volume concentration of about 20%, the preferred wavelength to be used in the method of this invention is from 750 to 850 nm. For a latex paint having a $TiO_2$ volume concentration of about 30%, the preferred wavelength for measurement is 850 to 1000 nm.

Total transmittance of the sample is measured at the determined wavelength for the purpose of determining light scattering efficiency. The measured value of total transmittance is used to calculate optical density and subsequently scattering efficiency of the pigment, as described below.

Undertone in an end-use application is determined by comparing light scattering at the lower end of the visible spectrum ($\lambda_1$=blue wavelength) to scattering at the upper end of the visible spectrum ($\lambda_2$=red wavelength). To determine undertone in dilute pigment slurries, these wavelengths both need to be shifted higher, just as the wavelength used to characterize optical density or opacification performance is shifted higher. Instead of a blue wavelength, total transmittance of the sample is measured using a first wavelength, $\lambda_1$, in the range of 500 to 650 nm and instead of red light, total transmittance is measured using a second wavelength, $\lambda_2$, in the range of 650 to 1000 nm. Optical densities are calculated at each wavelength from the measurements of total transmittance. The optical densities are used to calculate the undertone of the pigment, as described below. Optical density typically decreases as the measuring wavelength increases. Pigments having curves of optical density versus wavelength with steeper declines as wavelength increases correspond to those having higher undertone values.

Optionally a "blank" run is made prior to measuring the total transmittance of the dilute pigment slurry sample to calibrate the instrument at each wavelength. To run a "blank", a spectrophotometer cell should be filled with the same continuous liquid medium, i. e., water, solvent or resin, used to prepare the dilute pigment slurry.

Surprisingly, the combination of measuring total transmittance, which includes both regular and diffuse transmittance, and taking the measurement at a wavelength greater than 600 nm, provides excellent correlation between optical density and the opacification performance, i. e., scattering efficiency in an end-use application.

Calculations

Optical density (OD) should be calculated from total transmittance (T) at each wavelength based on equation 1.

$$OD = -\log(T) \tag{1}$$

Concentration of the pigment in the slurry sample, C, in ppm, is known from sample preparation. By dividing by the concentration, light scattering efficiency can be calculated using equation 2.

$$\text{light scattering efficiency} = 10^6 \times \frac{OD}{C} \qquad (2)$$

For convenience and reliability, the optical density or light scattering efficiency can be reported relative to a standard pigment having a known value. In this way the optical properties of a standard pigment can be used for comparison with other sample pigments.

Undertone is calculated from the light scattering efficiencies calculated as described above at two wavelengths, $\lambda_1$ and $\lambda_2$. Many relationships can be used to characterize the rate of change of optical density with wavelength, but the logarithmic relationship of equation 3 is preferred:

$$\text{undertone} = -\frac{\left[\ln\frac{OD_1/C \text{ at } \lambda_1}{OD_2/C \text{ at } \lambda_2}\right]}{\left[\ln\frac{\lambda_1}{\lambda_2}\right]} \qquad (3)$$

$OD_1/C$ at $\lambda_1$ is the optical density calculated from the transmittance measurement at wavelength $\lambda_1$, divided by pigment concentration in the slurry. $OD_2/C$ at $\lambda_2$ is the optical density calculated from the transmittance measurement at wavelength $\lambda_2$, divided by pigment concentration in the slurry. For convenience, a scale factor can be included, if desired.

An alternative to equation 3 to provide undertone is provided in equation 4.

$$\text{undertone} = -\frac{(OD_1/C \text{ at } \lambda_1) - (OD_2/C \text{ at } \lambda_2)}{\lambda_1 - \lambda_2} \qquad (4)$$

While calculated undertone values determined by the optical density determinations of this method may vary from conventional carbon black undertone (CBU) values, the results are consistent with each other in predicting the relative undertones for a group of pigments. CBU is described by Schaumann in U.S. Pat. No. 2,488,439, the teachings of which are incorporated herein by reference. The method of this invention to determine undertone is more rapid that the method described by Schaumann, which involves preparing oil mulls of a sample and a standard pigment with carbon black and comparing with a standard set of values. It has been found that calculated undertone values vary linearly with CBU and undertone values determined from optical density can be converted to the CBU-scale using the regression constants for this linear relationship.

Correlation with End-Use Performance

Assessment of end-use performance is not always readily available to intermediates manufacturers, nor are manufacturers of the end product often willing to test a new product without strong indication/support that the new product will provide an advantage to their process and/or their product. Therefore tests which provide good correlations with end-use performance are invaluable in product development, process control in pigment manufacture, and introduction to the market.

Measurement of pigment properties that correspond with end-use performance can be of assistance to both pigment manufacturers and their customers to improve formulations. A test based on spectrophotometric measurements taken of paint films or paper coatings deposited on plastic sheets provides results that reliably correspond with end-use performance. Such a test is described by Abrams, et al., in "Proceedings of 1996 TAPPI Coating Conference", described above. For example in this test, improvements in scattering efficiency can be directly correlated with equal or improved optical performance at reduced levels of $TiO_2$. However this test is time consuming. Replication error is better than most tests on end-use products but is still greater than 2%. Nonetheless, given the success of the test described by Abrams, et al., this test can be used for comparison with results obtained by the test method of this invention to support correlation with end-use performance.

The method of this invention is an improvement on the method described by Abrams, et al., for determining hiding power or light scattering efficiency of pigments. In the Abrams method, a coating formulation containing a particular pigment is prepared and coated onto a polyester film. The hiding power of the pigment is determined by measuring transmittance and reflectance of the film at a wavelength of 550 nm, followed by calculations that consider porosity of the coating. Surprisingly it has been found that determination of optical density via total transmittance measurements of a white pigment dispersed in a continuous liquid medium, when the transmittance measurement is made at a wavelength greater than 600 nm, provides results which correlate 1:1 with results from the method of Abrams, et al. Therefore, the present invention provides a simple test with results that correlate with performance of the pigment in an end-use application. Replication error by the method of this invention is only 0.5% which is a substantial improvement over the 2%+ error of the method of Abrams, et al.

Industrial Applications

The methods of this invention to determine light scattering efficiency and undertone of white pigments are useful to both pigment manufacturers and consumers. For example, these methods can be used in screening of pigments for various end-uses, in product and process development of pigments, and in optimizing formulations containing pigments.

Screening of pigments to compare light scattering efficiency and undertone can find utility in comparison of pigments to determine relative properties. Pigments can be evaluated, for example, for a particular scattering efficiency or for a desired undertone. As the results correlate with end-use performance, pigment consumers may gain benefit to understand which pigments are preferred in their products and formulations.

Screening of pigments is also useful to consumers in optimizing their formulations, for example, based on opacity. Less of a pigment having a higher light scattering efficiency may be used in place of a pigment having a lower light scattering efficiency resulting in the same opacity at a lower cost of manufacture. Alternatively, higher opacity may be achieved by replacing a pigment with a pigment having a higher light scattering efficiency.

In the manufacture of titanium dioxide pigments, by either the sulfate or chloride process, the pigment products are in the form of agglomerates and aggregates of $TiO_2$ crystals. Undertone measurements according to the method of this invention can be used to optimize the size of the crystals. Optical density measurements according to the method of this invention can be used to optimize the degree of agglomeration. These methods can be used as tools for quality control in the pigment manufacturing process. In contrast, conventional quality control methods, such as those based on particle size, cannot differentiate effects of crystal size and degree of agglomeration.

Crystal size is generally determined in the calciner for sulfate process and in the oxidation step of the chloride process. Degree of agglomeration is affected by grinding and milling steps. Understanding and controlling crystal size and agglomeration can be useful in new product development and process improvements.

Undertone is particularly important where color matching is critical, such as in color mixing of paints, in automotive refinishing, and matching of colored materials from different sources. Therefore the methods of this invention can readily provide manufacturers of $TiO_2$ pigments with information relating to quality of their pigment products and further assist their customers with formulations.

DETAILED DESCRIPTION OF THE FIGURES

FIG. 1 shows a graph of relative optical density over concentration (OD/C) versus relative scattering coefficient (S) in an end-use formulation for paper coatings for a series of titanium dioxide pigments, described in the Examples, Table 1. Relative optical densities were determined using the method of this invention. Relative S values for the same pigments were determined using the method described by Abrams, et al, wherein paint formulations were deposited on Mylar® polyester sheets. The line drawn in the graph is the ideal 1:1 correlation line. When optical density is measured at 700 nm, the data closely follow the 1:1 correlation line. When optical density is monitored at the conventional green wavelength (550 nm), the performance is frequently over-predicted.

Figure 2:
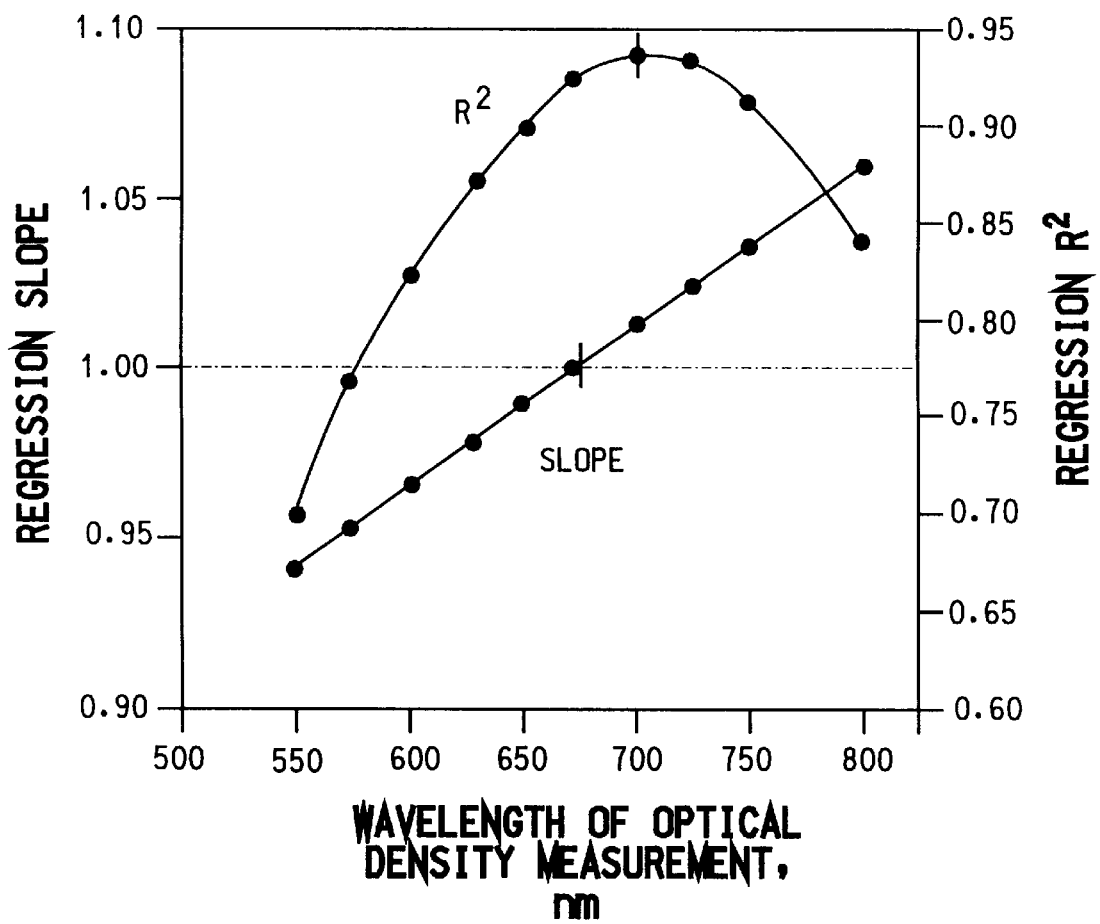
FIG. 2 is a graph showing correlation of relative optical densities with scattering coefficients in a paper coating and the related regression $R^2$ values.

FIG. 2 shows a graph of regression slope and regression $R^2$ versus wavelength for optical density determinations. This graph is useful to select preferred wavelengths to measure total transmittance for the method of this invention for a paper coating end-use application. Total transmittance is measured at a number of wavelengths. Results for relative optical density over concentration (OD/C) are compared with relative scattering coefficients (S), determined by the method of Abrams, et al. The graph shows the linear regression slope of relative OD/C versus relative S for a number of wavelengths and the corresponding regression $R^2$ values. As can be seen from the graph, there is a 1:1 correlation (slope=1) and the highest $R^2$ values at a wavelength of about 700 nm.

FIG. 2 provides information to select preferred wavelengths for correlating measurements with performance in paper coatings. Similar comparisons of relative optical density/concentration with scattering coefficients, S, can be made by those skilled in the art for other end-use applications to select preferred wavelengths for measurements to correlate with end-use performance. Other end-use applications include pigment-filled paper, plastics, and paints.

EXAMPLES

Example 1

To demonstrate the ability of the test method of this invention to provide results that correlate with end-use performance, measurements were taken of a series of commercial titanium dioxide pigments described in Table 1.

TABLE 1

| Pigment Sample | Crystal Form | Primary Crystal Size, microns (a) | Aggregate Size, microns (b) | Degree of Agglomeration (c) |
|---|---|---|---|---|
| A | Anatase | 0.140 | 0.68 | 4.3 |
| B | Rutile | 0.213 | 0.48 | 2.3 |

TABLE 1-continued

| Pigment Sample | Crystal Form | Primary Crystal Size, microns (a) | Aggregate Size, microns (b) | Degree of Agglomeration (c) |
|---|---|---|---|---|
| C | Rutile | 0.172 | 0.40 | 2.3 |
| D | Rutile | 0.205 | 0.39 | 1.9 |
| E | Rutile | 0.195 | 0.31 | 1.6 |

(a) Primary crystal size is determined by electron microscopy.
(b) Aggregate size is determined using a Horiba LA-900 laser scattering particle size analyzer (available from Horiba Instruments, Inc., Irvine, California).
(c) Degree of agglomeration is the ratio of aggregate size to primary particle size.

Anatase pigment A was prepared by the sulfate process. Rutile pigments B–E were prepared by the chloride process. For the rutile pigments, differences in primary crystal size were achieved by varying nucleant as described by Lewis and Braun in U.S. Pat. No. 3,208,866 and Allen and Evers in U.S. Pat. No. 5,201,949. Differences in aggregate size were achieved by flue design as described by Gonzalez in U.S. Pat. No. 4,937,064 and by Gonzalez and Musick in U.S. Pat. No. 5,538,708 and by grinding as described by Ott and Sullivan in U.S. Pat. No. 5,356,470 and by Ott, et al., in U.S. Pat. No. 5,653,793.

A dilute aqueous slurry having a $TiO_2$ concentration of 20 ppm was prepared for each of the sample pigments. The water used for dilution contained 0.016 g/l of(tetrapotassium pyrophosphate) TKPP as a dispersant.

Total transmission for each of the samples was measured using a 1-cm path length cell on a Hunter Ultrascan spectrophotometer (available from HunterLab, Reston, Va.) which is equipped with an integrating sphere to provide analysis of total transmittance. Measurements were recorded at wavelengths of 550 and 700 nm.

Optical density for each sample was calculated using equation 1. Scattering efficiency was calculated using equation 2. Optical densities using sample B as a standard are provided in Table 2.

TABLE 2

| Pigment Sample | Relative Scattering Efficiency (Relative Optical Density/Concentration) | | Relative $S_{TiO2}$ in Paper Coating |
|---|---|---|---|
| | @ 550 nm | @ 700 nm | |
| A | 0.89 | 0.80 | 0.79 |
| B | 1 | 1 | 1 |
| C | 1.18 | 0.99 | 0.99 |
| D | 1.18 | 1.10 | 1.08 |
| E | 1.22 | 1.15 | 1.14 |

As can be seen from the data in Table 2, and in FIG. 1, the relative scattering efficiency (optical density/concentration), based on measurement at 700 nm correlates much better with the relative scattering coefficient (S) in the end-use, than relative optical density/concentration, based on measurement at 550 nm. Therefore, scattering efficiencies based on transmittance measurements at 700 nm will correlate with performance of these pigments in end-use applications.

For comparison, total transmission for each of the samples was measured without an integrating sphere to provide analysis of only regular transmittance. Measurements were recorded at wavelengths of 550 and 700 nm.

Optical density for each sample was calculated using equation 1. Scattering efficiency was calculated using equation 2. Optical densities using sample B as a standard are provided in Table 3.

TABLE 3

| Pigment Sample | Relative Scattering Efficiency (Relative Optical Density/Concentration) | | Relative $S_{TiO2}$ in Paper Coating |
|---|---|---|---|
| | @ 550 nm | @ 700 nm | |
| A | 1.00 | 0.86 | 0.79 |
| B | 1 | 1 | 1 |
| C | 1.12 | 1.03 | 0.99 |
| E | 1.14 | 1.04 | 1.14 |

As can be seen from Table 3, when an integrating sphere is not used, that is, there is not a measurement of total transmittance, only regular transmittance, neither measurements at 550 nm nor 700 nm provide data which correlates with performance. Performance is based on Relative $S_{TiO2}$ as determined by the method of Abrams, et al. The results based on regular transmittance only with a measurement at 550 nm over-predict the relative performance of pigments A and C. The results based on regular transmittance only with a measurement at 700 nm over-predict performance of pigment A and under-predict performance of pigments C and E. There is no wavelength which provides a 1:1 correlation of Relative Scattering Efficiency (Relative Optical Density/Concentration) with relative $S_{TiO2}$.

Undertones calculated according to equation 3 are provided in Table 4. Also included in Table 4 for comparison are CBU values, as determined by the method of Schaumann.

TABLE 4

| Pigment Sample | Undertone | CBU |
|---|---|---|
| A | 0.86 | 15 |
| B | 0.47 | 12 |
| C | 1.18 | 18 |
| D | 0.74 | 14 |
| E | 0.69 | 14 |

As can be seen from Table 4, the undertone values determined using the method of this invention correlate with CBU values determined in accordance with the method of Schaumann.

Example 2

Industrial scale trials were performed at a series of paper mills to test rutile pigment B and rutile pigment D, which are described above. The trial included mills producing coated freesheet, coated groundwood, and coated paperboard. Coated freesheet papers are made using pulp fibers that have been chemically treated to remove lignin. Coated groundwood papers use 10% or more of mechanical pulps. The term "lightweight coated" (LWC) is often used interchangeably with coated groundwood. The grade structure and manufacture of these papers are described in "Pulp and Paper 1997 North American Fact Book", Miller Freeman, Inc., San Francisco (1996), pages 183–195. The coated paperboard trials included both coated unbleached kraft ("Pulp and Paper 1997 North American Fact Book", pages 297–301.) and coated recycle board ("Pulp and Paper 1997 North American Fact Book", pages 303–314.).

$TiO_2$ scattering efficiencies were determined using measurements of coat weight, $TiO_2$ content, opacity and reflectance in the green region of the visible spectrum. The $TiO_2$ scattering coefficients were calculated by the method of McGinnis in TAPPI 1990 Coating Conference Proceedings, TAPPI Press, Atlanta, p. 23.

Light scattering efficiencies of the $TiO_2$ in coated paper samples were compared as pigment B was replaced with pigment D. The predicted scattering efficiency improvement achieved by replacing pigment B with pigment D based on the test method of this invention was 10%. (In Table 2, pigment B was used as a standard for comparison and assigned a relative scattering efficiency of 1, when transmittance was measured at 700 nm. Pigment D had a relative scattering efficiency of 1.10, when transmittance was measured at 700 nm.) Scattering efficiency was also determined by the method of Abrams, et al. Based on this method, the predicted scattering improvement achieved by replacing pigment B with Pigment D was 8%.

Tables 5 to 7 provides data for scattering efficiency improvement based on mill performance.

TABLE 5

| Coated Freesheet Mills | Scattering Efficiency Improvement |
|---|---|
| 1 | 8–12% |
| 2 | 7% |
| 3 | 4% |
| 4 | 10% |
| Average | 8% |

TABLE 6

| Coated Groundwood Mills | Scattering Efficiency Improvement |
|---|---|
| 5 | 8% |
| 6 | 7% |
| 7 | 7% |
| Average | 7% |

TABLE 7

| Coated Paperboard Mills | Scattering Efficiency Improvement |
|---|---|
| 8 | 8% |
| 9 | 8% |
| 10 | 7% |
| 11 | 9% |
| 12 | 12% |
| 13 | 11% |
| 14 | 5% |
| Average | 9% |

As can be seen from Tables 5 to 7, there is an improvement of 7–9% for the mill trials, which supports the test method of this invention as a quick and simple for predicting light scattering efficiency. It should also be noted that using a conventional wavelength in the green region for the optical density determination (550 nm, see Table 2), the improvement in scattering efficiency is over-predicted at 18%.

What is claimed is:

1. A method to determine light scattering efficiency of a white pigment wherein the light scattering efficiency correlates with performance in an end-use application, comprising:

(a) preparing a dilute slurry of a pigment in a continuous liquid medium having a known concentration, where concentration is the concentration of pigment in the slurry;

(b) measuring the total transmittance (T) of the slurry at a wavelength ($\lambda$) of at least 600 nm;

(c) converting the transmittance measurement (T) to optical density (OD) by the equation $$OD = -\log(T)$$

and (d) dividing the optical density by the concentration of the pigment in the slurry to determine light scattering efficiency of the pigment.

2. The method of claim 1 wherein the continuous medium is selected from the group consisting of water, organic solvents, and paint resins.

3. The method of claim 2 wherein the continuous medium is water.

4. The method of claim 1 wherein the pigment is selected from the group consisting of rutile titanium dioxide, anatase titanium dioxide, zinc oxide, silica, calcium carbonate, calcium sulfate and clay, and mixtures thereof.

5. The method of claim 3 wherein the pigment is selected from the group consisting of rutile titanium dioxide and anatase titanium dioxide.

6. The method of claim 1 wherein the pigment is rutile titanium dioxide or anatase titanium dioxide and wherein the continuous medium is water.

7. The method of claim 3 wherein the end-use application is a pigment-filled paper and the wavelength is in the range of 600 to 700 nm.

8. The method of claim 3 wherein the end-use application is selected from the group consisting of paper coatings and plastics, and the wavelength is in the range of 650 to 750 nm.

9. The method of claim 3 wherein the end-use application is a paint, and the wavelength is in the range of 750 to 1000 nm.

10. The method of claim 9 wherein the paint is a latex paint having a $TiO_2$ volume concentration of about 20, and the wavelength is in the range of 750 to 850 nm.

11. The method of claim 9 wherein the paint is a latex paint having a $TiO_2$ volume concentration of about 30, and the wavelength is in the range of 850 to 1000 nm.

12. A method to determine undertone of a white pigment, comprising:

(a) preparing a dilute slurry of a pigment in a continuous medium having a known concentration (C), where concentration is the concentration of pigment in the slurry;

(b) measuring total transmittance ($T_1$) of the slurry at a wavelength, $\lambda_1$, between 500 and 650 nm;

(c) measuring total transmittance ($T_2$) of the slurry at a wavelength, $\lambda_2$, between 650 and 1000 nm;

(d) converting the transmittance measurements to optical densities (OD) by the equation $$OD = -\log(T)$$

(e) dividing the optical densities by the concentration (C) of the pigment in the slurry to calculate OD/C;

(f) determining the undertone of the pigment by the degree of change in OD/C between $\lambda_1$ and $\lambda_2$.

13. The method of claim 12 wherein the degree of change in OD/C is calculated according to the equation:

$$\text{undertone} = -\frac{\left[\ln\dfrac{OD_1/C \text{ at } \lambda_1}{OD_2/C \text{ at } \lambda_2}\right]}{\left[\ln\dfrac{\lambda_1}{\lambda_2}\right]},$$

wherein $OD_1/C$ at $\lambda_1$ is the optical density calculated from the transmittance measurement at wavelength $\lambda_1$, divided by the concentration of the pigment in the slurry and $OD_2/C$ at $\lambda_2$ is the optical density calculated from the transmittance measurement at wavelength $\lambda_2$, divided by the concentration of the pigment in the slurry.

14. The method of claim 12 wherein the degree of change in OD/C is calculated according to the equation:

$$\text{undertone} = -\frac{(OD_1/C \text{ at } \lambda_1 - OD_2/C \text{ at } \lambda_2)}{\lambda_1 - \lambda_2},$$

wherein $OD_1/C$ at $\lambda_1$ is the optical density calculated from the transmittance measurement at wavelength $\lambda_1$, divided by the concentration of the pigment in the slurry and $OD_2/C$ at $\lambda_2$ is the optical density calculated from the transmittance measurement at wavelength $\lambda_2$, divided by the concentration of the pigment in the slurry.

15. The method of claim 1 further comprising determining light scattering efficiency for each of a series of pigments as a method to screen pigments to determine relative light scattering efficiencies of the pigments.

16. The method of claim 12 further comprising determining undertone for each of a series of pigments as a method to determine undertone for color matching.

* * * * *